United States Patent [19]
Urich

[11] Patent Number: 5,879,363
[45] Date of Patent: *Mar. 9, 1999

[54] DISPOSABLE SURGICAL ULTRASONIC TRANSDUCER

[75] Inventor: Alex Urich, Mission Viejo, Calif.

[73] Assignee: Circuit Tree Medical, Inc., Mission Viejo, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 819,301

[22] Filed: Mar. 18, 1997

[51] Int. Cl.$^6$ .................................................. A61B 17/32
[52] U.S. Cl. .............................................. 606/167; 604/22
[58] Field of Search ..................... 606/167, 169; 604/22

[56] References Cited

U.S. PATENT DOCUMENTS

| | | | |
|---|---|---|---|
| 4,425,115 | 1/1984 | Wuchinich | 606/169 |
| 5,167,725 | 12/1992 | Clark et al. | 606/169 |
| 5,312,329 | 5/1994 | Beaty et al. | 604/22 |
| 5,324,297 | 6/1994 | Hood et al. | 606/169 |
| 5,342,380 | 8/1994 | Hood | 606/169 |
| 5,391,144 | 2/1995 | Sakurai et al. | 606/169 |

*Primary Examiner*—Michael Buiz
*Assistant Examiner*—Daphna Shai
*Attorney, Agent, or Firm*—Blakely Sokoloff Taylor & Zafman

[57] ABSTRACT

An ultrasonic surgical instrument that has a disposable piezoelectric driver. The surgical instrument includes an ultrasonic horn that is attached to an outer handle. A surgical tip or blade is attached to the proximal end of the horn. The piezoelectric driver is attached to the distal end of the horn. The driver contains at least one piezoelectric transducer which creates a vibratory movement of the horn and the surgical tip. The piezoelectric driver and ultrasonic horn are attached by corresponding threaded members or other means for mechanically coupling the devices so that the driver can be detached from the horn. The piezoelectric driver is disconnected from the horn after use in a surgical procedure. The horn and handle are then sterilized. A new piezoelectric driver is then attached to the horn for use in another procedure.

15 Claims, 1 Drawing Sheet

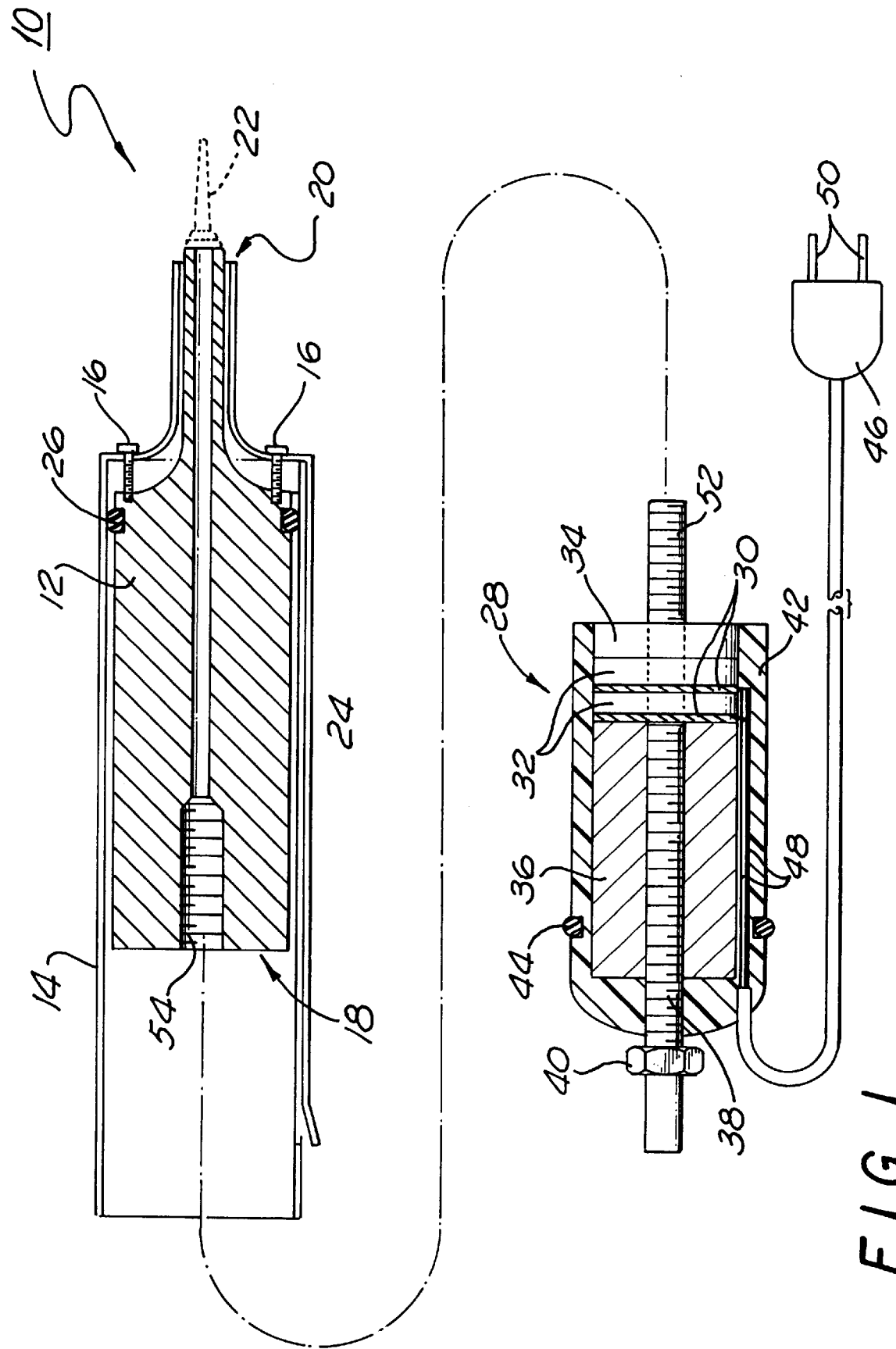

DISPOSABLE SURGICAL ULTRASONIC TRANSDUCER

BACKGROUND OF THE INVENTION

1. Field of the Invention

The present invention relates to an ultrasonic surgical instrument which has a disposable piezoelectric driver that is detachably connected to an ultrasonic horn.

2. Description of Related Art

Ultrasonic surgical devices are used to perform a variety of different surgical procedures. For example, ultrasonic instruments are used to break and remove a cataracteous lens from a cornea. The ultrasonic instrument typically includes a number of piezoelectric transducers that are mounted to an ultrasonic horn in a single horn assembly. The horn is attached to an outer handle that can be held by a surgeon. A tip or blade is typically attached to the proximal end of the horn. The piezoelectric elements are connected to a number of wires that provide electrical power to the instrument. The piezoelectric transducers convert the electrical energy into a mechanical vibratory movement of the horn and the tip. The vibratory movement of the horn induces a cutting action of the tip.

Ultrasonic instruments must be sterilized after each surgical procedure. Sterilization is typically accomplished by placing the handle, horn and piezoelectric transducers in an autoclave and subjecting the instrument to steam at high pressures and temperatures. It has been found that the high pressures and temperatures within the autoclave will degrade the performance characteristics of the piezoelectric transducers. For example it has been found that after no fewer than one autoclave cycle the electrical to mechanical energy conversion efficiency of the piezoelectric transducers will drop 50%. Because the ultrasonic horn and piezoelectric transducers are provided as one assembled component, both the horn and the transducers must be replaced by a new horn assembly, even though the horn is still functional.

The ultrasonic horns are typically precision devices that are constructed from a relatively expensive material such as titanium. The disposal of the transducers and horn results in an undesirable waste of the horn, which adds to the cost of performing a surgical procedure. Additionally, the output of the instrument during a surgical procedure is unpredictable because of the unknown degradation of the transducers. Some instruments incorporate elaborate monitor and feedback devices that sense the output of the piezoelectric transducers. These devices add to the cost and complexity of the instrument. It would be desirable to provide an ultrasonic surgical instrument that was immune to any degradation of performance because of exposure to autoclave sterilization.

SUMMARY OF THE INVENTION

The present invention is an ultrasonic surgical instrument that has a disposable piezoelectric driver. The surgical instrument includes an ultrasonic horn that is attached to an outer handle. A surgical tip or blade is attached to the proximal end of the horn. The piezoelectric driver is attached to the distal end of the horn. The driver contains at least one piezoelectric transducer which creates a vibratory movement of the horn and the surgical tip. The piezoelectric driver and ultrasonic horn are attached by corresponding threaded members or other means for mechanically coupling the devices so that the driver can be detached from the horn. The piezoelectric driver is disconnected from the horn after use in a surgical procedure. The horn and handle are then sterilized. A new piezoelectric driver is then attached to the horn for use in another procedure. With the two piece horn assembly of the present invention the same horn can be used in a large number of surgical procedures. The piezoelectric drivers are constructed as relatively inexpensive assemblies that can be disposed of while still minimizing the cost of the instrument per each surgical procedure.

BRIEF DESCRIPTION OF THE DRAWINGS

FIG. 1 is an exploded cross-sectional view of an ultrasonic surgical instrument of the present invention.

DETAILED DESCRIPTION OF THE INVENTION

Referring to the drawings more particularly by reference numbers, FIG. 1 shows an ultrasonic surgical instrument 10 of the present invention. The instrument 10 is typically held by a surgeon and used to perform surgical procedures such as the removal of a cataracteous lens.

The instrument 10 includes an ultrasonic horn 12 that is attached to an outer handle 14. The horn 12 may be attached to the handle 14 by a number of set screws 16. The ultrasonic horn 12 is attached to the outer handle 14 at a zero amplitude node of the horn 12 to prevent vibration of the handle 14. The ultrasonic horn 12 has a stepped reduction in area to provide an amplification of a vibratory movement of the horn 12. Although a stepped horn 12 is shown and described, it is to be understood that the horn 12 may have other shapes which promote an amplification of the displacement amplitude. In the preferred embodiment the length of the horn 12 is 0.5 to 2 inches. The large area of the horn 12 may be between 0.25 and 1.25 inches and the stepped area ratio may be between 1:2 to 1:50.

The horn 12 has a distal end 18 and a proximal end 20. A surgical tip 22 is attached to the proximal end 20 of the horn 12. Although a tip 22 is shown and described, it is to be understood that a blade or other surgical device can be attached to the horn 12. The outer handle 14 may have an irrigation line 24 that provides an irrigation fluid to the surgical site. The line 24 may be sealed by an O-ring 26.

The surgical instrument 10 further has a piezoelectric driver 28 that is attached to the distal end 18 of the horn 12. The piezoelectric driver 28 creates a vibratory movement of the horn 12 and the surgical tip 22. The piezoelectric driver 28 is provided as a separate relatively inexpensive disposable component that can be attached to, and disconnected from, the horn 12.

In the preferred embodiment, the piezoelectric driver 28 includes a pair of piezoelectric transducers 30. Although a pair of piezoelectric transducers 30 are shown, it is to be understood that the driver 28 may have only one transducer 30. The transducers 30 are clamped onto a disk 32 by a pair of washers 34 and a cylindrical block 36. A threaded rod 38 extends from the disk 32. The threads of the rod 38 cooperate with internal threads of the cylindrical block 36. Rotation of the rod 38 will move the block 36 toward the disk 32 to clamp the transducers 30. A hex nut 40 may be attached to the rod 38 to assist in the clamping of the transducers 30. The assembly is enclosed by an outer plastic housing 42 after the transducers 30 are clamped in place. An O-ring 44 may be attached to the housing 42 to seal the driver 28 within the handle 14 and prevent moisture from contaminating the transducers 30.

The transducers 30 are connected to an electrical connector 46 by a pair of wires 48. The connector 46 is mated with a corresponding connector (not shown) of a power supply (not shown) which provides power to the transducers 30. The transducers 30 convert the electrical energy into a mechanical movement of the disk 32. The connector 46 preferably contains only two electrical contacts 50 that are dedicated to electrical power and ground. Having only two electrical contacts reduces the complexity and cost of both the connector 46 on the driver and the corresponding connector of the power supply.

The disk 32 of the driver 28 preferably has an externally threaded rod 52 which is screwed into a corresponding internally threaded aperture 54 located at the distal end 18 of the horn 12. The user can utilize the hex nut 40 to screw the driver 28 into the horn 12. The driver 28 can be attached to the horn 12 with a wrench (now shown) which has a brake torque setting between 10–50 in-lb. The threaded members 52 and 54 allow a surgeon to readily attached and disconnect the piezoelectric driver 28 and the horn 12. Although threaded members 52 and 54 are shown and described, it is to be understood that the driver 28 may be detachably connected to the horn 12 by other mechanical coupling means. For example, the driver 28 can be attached to the horn 12 by a spring loaded latch.

In operation, the piezoelectric driver 28 is attached to the horn 12. Power is provided to the transducers 30 which convert the electrical energy into a vibratory movement of the horn 12 and the tip 22. The vibrating tip 22 is used to perform a surgical procedure. After the procedure, the driver 28 can be detached from the horn 12, removed from the instrument 10 and disposed of in a waste container.

The handle 14 and horn 12 are then sterilized, preferably by exposing the parts to steam within an autoclave. A new piezoelectric driver 28 is then attached to the horn 12 for use in another surgical procedure. The new driver 28 can be sterilized by gamma radiation or other nondestructive means and provided in a sterile package for shipment to a surgical site. It has been found that the mechanical coupling between the ultrasonic horn 12 and the piezoelectric driver 28 is sufficient even though the horn 12 and driver 28 are merely screwed together by an end user. There is no requirement for constructing the horn 12 and driver 28 as one piece as was done in the prior art. Consequently, the horn 12 can be used for a large number of surgical procedures.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An ultrasonic surgical instrument, comprising:
   an ultrasonic horn;
   a piezoelectric driver that moves said ultrasonic horn in a vibratory manner, said piezoelectric driver contains a piezoelectric transducer which is clamped between a block and a washer, and a housing that covers said piezoelectric transducer, said block and said washer, said piezoelectric driver being mechanically coupled to said horn so that said piezoelectric transducer, said block, said washer and said housing can be separated from said horn as a single unit; and,
   a handle that at least partially encloses said ultrasonic horn and said piezoelectric driver.

2. The instrument as recited in claim 1, wherein said piezoelectric driver is mechanically coupled to said horn by a pair of corresponding threads.

3. The instrument as recited in claim 1, further comprising a handle that is attached to said horn.

4. The instrument as recited in claim 1, wherein said piezoelectric driver includes at least one piezoelectric transducer that is connected to an electrical connector.

5. The instrument as recited in claim 4, wherein said electrical connector consist of at least two electrical contacts.

6. The instrument as recited in claim 4, wherein said piezoelectric driver includes a plastic housing.

7. The instrument as recited in claim 3, wherein said handle includes an irrigation line.

8. The instrument as recited in claim 1, further comprising a surgical tip that is attached to said horn.

9. An ultrasonic surgical instrument, comprising:
   a handle;
   an ultrasonic horn that is attached to said handle by a screw which prevents rotation of said ultrasonic horn relative to said handle;
   a surgical tip that is attached to said horn;
   a piezoelectric driver that is mechanically coupled to said horn so that said piezoelectric driver can be separated from said horn, said piezoelectric driver moves said horn and said surgical tip in a vibratory manner.

10. The instrument as recited in claim 9, wherein said piezoelectric driver is mechanically coupled to said horn by a pair of corresponding threads.

11. The instrument as recited in claim 9, wherein said piezoelectric driver includes a piezoelectric transducer that is connected to an electrical connector.

12. The instrument as recited in claim 11, wherein said electrical connector consist of two electrical contacts.

13. The instrument as recited in claim 11, wherein said piezoelectric driver includes a plastic housing.

14. The instrument as recited in claim 9, wherein said handle includes an irrigation line.

15. A method for assembling an ultrasonic surgical instrument, comprising the steps of:
    a) clamping a piezoelectric transducer between a block and a washer;
    b) enclosing said piezoelectric transducer, said washer and said block in a housing; and,
    c) attaching said housing enclosed piezoelectric transducer, said washer and said block to a horn that is partially inclosed by a handle.

* * * * *